(12) United States Patent
Wenger et al.

(10) Patent No.: US 7,213,469 B2
(45) Date of Patent: May 8, 2007

(54) VIBRATORY TRANSDUCER FOR CORIOLIS MASS FLOWMETER OR A CORIOLIS MASS FLOWMETER-DENSIMETER

(75) Inventors: Alfred Wenger, Neftenbach (CH); Martin Anklin, Aesch (CH)

(73) Assignee: Endress + Hauser Flowtec AG, Reinach (CH)

( * ) Notice: Subject to any disclaimer, the term of this patent is extended or adjusted under 35 U.S.C. 154(b) by 0 days.

(21) Appl. No.: 11/415,176

(22) Filed: May 2, 2006

(65) Prior Publication Data

US 2006/0196279 A1   Sep. 7, 2006

Related U.S. Application Data

(63) Continuation of application No. 11/139,643, filed on May 31, 2005, now Pat. No. 7,062,977, which is a continuation of application No. 10/252,114, filed on Sep. 23, 2002, now Pat. No. 6,920,798.

(60) Provisional application No. 60/330,616, filed on Oct. 26, 2001.

(30) Foreign Application Priority Data

| Sep. 21, 2001 | (EP) | ................................. | 01122801 |
| Oct. 29, 2001 | (EP) | ................................. | 01125774 |

(51) Int. Cl.
  *G01F 1/84* (2006.01)
(52) U.S. Cl. ............................... 73/861.355
(58) Field of Classification Search ..................... None
  See application file for complete search history.

(56) References Cited

U.S. PATENT DOCUMENTS

| 4,711,132 | A | 12/1987 | Dahlin |
| 4,831,885 | A | 5/1989 | Dahlin |
| 5,370,002 | A | 12/1994 | Normen |
| 5,540,106 | A | 7/1996 | Lew |
| 5,576,500 | A | 11/1996 | Cage |
| 5,616,868 | A | 4/1997 | Hagenmeyer |
| 5,731,527 | A | 3/1998 | Van Cleve |
| 6,711,958 | B2 | 3/2004 | Bitto |
| 6,920,798 | B2 * | 7/2005 | Wenger et al. ......... 73/861.355 |
| 7,062,977 | B2 * | 6/2006 | Wenger et al. ......... 73/861.355 |

FOREIGN PATENT DOCUMENTS

WO   WO 92/19940   11/1992

* cited by examiner

*Primary Examiner*—Harshad Patel
(74) *Attorney, Agent, or Firm*—Bacon & Thomas, PLLC

(57) ABSTRACT

A transducer has at least one at least temporarily vibrating flow tube of predeterminable lumen for conducting a fluid. The flow tube communicates with a connected pipe via an inlet tube section (103), ending in an inlet end, and an outlet tube section, ending in an outlet end, and in operation performs flexural vibrations about an axis of vibration joining the inlet and outlet ends. The flow tube has at least one arcuate tube section of predeterminable three-dimensional shape which adjoins a straight tube segment on the inlet side and a straight tube segment on the outlet side. At least one stiffening element is fixed directly on or in close proximity to the arcuate tube segment to stabilize the three-dimensional shape. By means of the at least one stiffening element, the cross sensitivity of the transducer is greatly reduced, so that cross talks from pressure to mass flow signals are minimized and the accuracy of the transducer is improved.

25 Claims, 3 Drawing Sheets

VIBRATORY TRANSDUCER FOR CORIOLIS MASS FLOWMETER OR A CORIOLIS MASS FLOWMETER-DENSIMETER

This application is a continuation of U.S. Ser. No. 11/139,643 filed on May 31, 2005 now U.S. Pat. No. 7,062,977, which is a continuation of U.S. Ser. No. 10/252,114 filed on Sep. 23, 2002 now U.S. Pat. No. 6,920,798, which is a nonprovisional application based on Provisional Application No. 60/330,616, filed on Oct. 26, 2001.

FIELD OF THE INVENTION

This invention relates to a vibratory transducer which is particularly suited for a Coriolis mass flowmeter or a Coriolis mass flowmeter-densimeter.

BACKGROUND OF THE INVENTION

In measurement and automation technology, the mass flow rate and/or the density of a fluid flowing in a pipe, particularly of a liquid, are frequently determined by means of meters which, using a vibratory transducer and a measuring and control circuit connected thereto, induce reaction forces, particularly Coriolis forces corresponding to the mass flow rate and inertia forces corresponding to the density, in the fluid flowing through the transducer and derive therefrom a measurement signal representing the respective mass flow rate and/or the respective density of the fluid.

Such Coriolis mass flowmeters or Coriolis mass flowmeter-densimeters are disclosed, for example, in WO-A 01/33174, WO-A 00/57141, WO-A 98/07009, U.S. Pat. No. 5,796,011, U.S. Pat. No. 5,731,527, U.S. Pat. No. 4,895,030, U.S. Pat. No. 4,781,069, EP-A 1 001 254, EP-A 553 939, or EP-A 1 154 243. Each of those Coriolis mass flowmeters or Coriolis mass flowmeter-densimeters provides corresponding measurement signals using a vibratory transducer comprising at least one flow tube of predeterminable lumen which serves to conduct a fluid, has an inlet end and an outlet end, is curved at least in segments, and vibrates at least temporarily, and which, to permit flow of the fluid therethrough, communicates with a connected pipe via an inlet tube section, ending in the inlet end, and an outlet tube section, ending in the outlet end, and in operation, in order to deform the lumen of the flow tube, performs flexural vibrations about a first axis of vibration, which joins the inlet and outlet ends.

To generate and maintain the vibrations of the at least one flow tube, each of the transducers is provided with at least one excitation assembly which is energized by the aforementioned measuring and control circuit. The excitation assembly comprises a first, preferably electrodynamic or electromagnetic, vibration exciter, which in operation is traversed by an alternating, particularly bipolar, excitation current and which converts the excitation current into an excitation force acting on the flow tube.

Curved flow tubes, e.g., flow tubes bent into a U- or V-shape in a tube plane, particularly tubes of Coriolis mass flowmeters, are commonly excited in the so-called useful mode into cantilever vibrations so that the flow tubes, undergoing an elastic deformation, will oscillate about the transducer's first axis of vibration. To this end, the vibration exciter is generally positioned in the transducer in such a way as to act on the flow tube at an antinode of the useful mode, particularly at a midpoint region of the tube.

As a result of the cantilever vibrations about the longitudinal axis, Coriolis forces are induced in the fluid, which, in turn, result in cantilever vibrations of the so-called Coriolis mode being superimposed on the excited cantilever vibrations of the useful mode, the cantilever vibrations of the Coriolis mode being equal in frequency to those of the useful mode. In transducers of the kind described, these cantilever vibrations forced by Coriolis forces commonly correspond to torsional vibrations about a second axis of vibration, particularly an axis normal to the first axis, the second axis being essentially parallel to an imaginary vertical axis of the transducer.

With a curved tube shape, thermal expansion will cause practically no or only very slight mechanical stresses in the flow tube itself and/or in the connected pipe, particularly if materials with a high thermal expansion coefficient are used. Furthermore, the flow tube can be made long, particularly with a projecting portion, so that despite a relatively short mounting length, particularly at relatively low excitation power, high sensitivity of the transducer to the mass flow rate to be measured can be achieved.

The aforementioned circumstances also allow the flow tube or flow tubes to be made from materials with a high thermal expansion coefficient and/or a high modulus of elasticity, such as special steel.

The two parallel, essentially identically shaped flow tubes of the transducers disclosed in U.S. Pat. No. 5,796,001 and WO-A 01/33174 are essentially continuously curved, i.e., they are not straight practically anywhere.

By contrast, the flow tubes of the transducers shown in U.S. Pat. No. 5,731,527, U.S. Pat. No. 5,301,557, U.S. Pat. No. 4,895,030, WO-A 00/57141, WO-A 01/33174 or EP-A 1 154 243, for example, each have at least two straight tube segments which are connected via an arcuate tube segment, particularly a circular-arc-shaped segment. Compared to continuously curved flow tubes, such curved flow tubes with straight tube segments have the advantage that they can be manufactured at low cost by means of very simple bending tools. While continuously curved flow tubes generally have projecting arcuate tube segments and in most cases segments with different radii of curvature, flow tubes with straight tube segments can also be made using arcuate tube segments that have a single radius of curvature and/or comparatively small radii of curvature.

Preferably, the flow tubes are vibrated in operation at a natural instantaneous resonance frequency, particularly with the vibration amplitude regulated at a constant value. As the natural resonance frequency is also dependent on the instantaneous density of the fluid, commercially available Coriolis mass flowmeters can also measure the density of moving fluids, for example.

To locally sense vibrations of the flow tube and generate corresponding sensor signals, each of the transducers includes a sensor arrangement comprising at least one inlet-side and at least one outlet-side, e.g., electrodynamic, vibration sensor. Because of the superposition of the useful mode and the Coriolis mode, the vibrations of the flow tube sensed by means of the sensor arrangement on the inlet and outlet sides, and hence the corresponding sensor signals, exhibit a phase difference which is also dependent on the mass flow rate.

By means of the above-mentioned measuring and control circuit, this phase difference can be measured in the manner familiar to those skilled in the art, namely directly or indirectly by determining an amplitude difference, for example, and be used to generate the measurement signal representative of the mass flow rate of the fluid. Furthermore, the measuring and control circuit can determine the density of the fluid by taking into account an instantaneous frequency of at least one of the two sensor signals.

As is well known, in operation, the transducer, particularly the at least one flow tube, besides being subjected to the above-described, desired reaction forces, is also acted on by other physical quantities, particularly by quantities that are not influenceable. For example, due to the thermal expansion of the flow tube, the temperature of the fluid, which in most cases cannot be maintained constant, automatically results in the transducer exhibiting, besides its sensitivity to the primary measurands, i.e., mass flow rate and density, a cross sensitivity to a temperature distribution currently existing in the transducer. To compensate for such temperature-induced perturbing effects on the measurement signals, Coriolis mass flowmeters or Coriolis mass flowmeter-densimeters commonly also incorporate at least one temperature sensor for measuring the temperature of the flow tube or of the environment about the tube, for example.

It is also known that such vibratory transducers, besides having the above-described sensitivity to a spatial and temporal temperature distribution existing inside the transducer, may exhibit a significant cross sensitivity to a static internal pressure existing in the lumen of the flow tube or to a pressure difference existing between the lumen and the environment of the tube. This fact is pointed out also in U.S. Pat. No. 5,731,527, U.S. Pat. No. 5,301,557, WO-A 95/16897, and WO-A 98/07009, for example. Such cross sensitivities can be accounted for by the fact that depending on the level of the internal pressure or on the magnitude of the pressure difference, the fluid counteracts the deformation of the vibrating flow tube with differently great forces.

Unfortunately, such cross sensitivities of the transducer to pressure may result in, mostly undesired, cross talks from pressure to mass flow corresponding Coriolis forces. To ensure the required high measurement accuracy, which generally should be at least within about ±0.15% of the actual mass flow rate or the actual density, additional measures are therefore necessary to compensate for the pressure dependence of the measurement signals, particularly if the internal pressure may vary over a wide range of, e.g., more than 5 bars.

To solve the problem, U.S. Pat. No. 5,301,557, for example, proposes to use flow tubes of comparatively great wall thickness in order to oppose the elastic deformations of the respective flow tube with a force which may be very high but is virtually constant. This, however, particularly because of the resulting increase in the mass of the flow tube, results in the transducer's sensitivity to the primary measurands, i.e., mass flow rate and density, being reduced along with the cross sensitivity to pressure. U.S. Pat. No. 5,731,527 proposes a similar solution in which the straight tube segments are provided with tubular stiffening elements of anisotropic, particularly glass-fiber-reinforced, materials, which stiffening elements serve to impart to the straight tube segments stiffnesses dependent on the orientation of the mechanical stresses acting in the respective tube segments, thus making the flow tube more pressure-resistant while maintaining good sensitivity to Coriolis forces.

Another possibility of reducing the transducer's cross sensitivity to pressure is described in WO-A 98/07009 or WO-A 95/16897. It is proposed to determine the internal pressure or the pressure difference during operation by means of resonance frequencies of two different, simultaneously or successively excited vibration modes of the at least one vibrating flow tube, and to take this internal pressure or pressure difference into account in the generation of the measurement signal representing the mass flow rate. To this end, the excitation assembly disclosed therein has, in addition to the usual single exciter, at least a second vibration exciter, which acts on the flow tube at a given distance from the first exciter. As is readily apparent, this involves an additional amount of mechanical complexity as well as a considerable additional amount of complexity of the measuring and control circuit, in which additional arithmetic capability must be provided. On the one hand, this substantially increases the manufacturing costs of such a Coriolis mass flowmeter-densimeter. On the other hand, such an increase in the complexity of both the installed hardware and the firmware implemented therein entails a disproportionate increase in error probability or even in the probability of failure and, thus, a substantial increase in the complexity of the monitoring necessary to ensure the required reliability of the Coriolis mass flowmeter-densimeter.

SUMMARY OF THE INVENTION

Starting from the above prior art, the invention therefore has for its object to provide a vibratory transducer suitable for use in a Coriolis mass flowmeter, particularly in a Coriolis mass flowmeter-densimeter, whose single flow tube or whose flow tubes are easy to manufacture and particularly easy to bend, and whose cross sensitivity to the internal pressure existing in its lumen, or to variations thereof, can be kept at a low level with comparatively simple and particularly low-cost means.

To attain this object, a first variant of the invention provides a vibratory transducer, particularly for producing mass-flow-rate-dependent Coriolis forces in moving fluids, having at least one at least temporarily vibrating flow tube of predeterminable lumen with an inlet end and an outlet end and serving to conduct a fluid. In order to permit flow of the fluid therethrough, the flow tube communicates with a connected pipe via an inlet tube section, ending in the inlet end, and via an outlet tube section, ending in the outlet end. In operation, the flow tube performs flexural vibrations about an axis of vibration joining the inlet and outlet ends in order to deform the lumen of the flow tube. Said flow tube having at least one arcuate tube segment of predeterminable three-dimensional shape which adjoins a first straight tube segment on the inlet side and a second straight tube segment on the outlet side. In order to stabilize the three-dimensional shape of the at least one arcuate tube segment, at least a first stiffening element is fixed on said arcuate tube segment.

A second variant of the invention provides a vibratory transducer, particularly for producing mass-flow-rate-dependent Coriolis forces in moving fluids, having at least one at least temporarily vibrating flow tube of predeterminable lumen with an inlet end and an outlet end and serving to conduct a fluid. In order to permit flow of the fluid therethrough, the flow tube communicates with a connected pipe via an inlet tube section, ending in the inlet end, and via an outlet tube section, ending in the outlet end. In operation, the flow tube performs flexural vibrations about an axis of vibration joining the inlet and outlet ends in order to deform the lumen of the flow tube. Said flow tube having at least one arcuate tube segment of predeterminable three-dimensional shape which adjoins a first straight tube segment on the inlet side and a second straight tube segment on the outlet side. In order to stabilize the three-dimensional shape of the at least one arcuate tube segment, at least a first stiffening element and at least a second stiffening element fixed on the first straight tube segment and the second straight tube segment, respectively.

In a first preferred embodiment of the invention, the at least first stiffening element is annular in shape and is fixed to the flow tube so as to encompass the latter.

In a second preferred embodiment of the invention, the at least first stiffening element encompasses the flow tube essentially coaxially.

In a third preferred embodiment of the invention, the flow tube has an inside diameter of more than 40 mm, particularly of more than 50 mm.

A fundamental idea of the invention is to keep the flow tube partially as dimensionally stable as possible in the particularly pressure-sensitive area of the at least one arcuate tube segment, at least in the cross section, through low-mass, local stiffening means, thus stabilizing practically the entire flow tube in such a manner that the deformations of the tube lumen caused by the flexural vibrations are nearly independent of the existing internal pressure or independent of the above-mentioned pressure difference. Since relatively small masses are added to the flow tube, whereby the total mass of the tube is kept low, the high sensitivity to the primary measurands, mass flow rate and density, which is achieved with conventional transducers is virtually preserved.

The invention is predicated on recognition that in the case of flow tubes curved in the manner described, the pressure dependence of the deformation is concentrated essentially on the comparatively short arcuate tube segments but may be so marked there that this effect cannot be left out of account in a high-precision determination of the primary measurands.

BRIEF DESCRIPTION OF THE DRAWINGS

The invention and further advantages will become more apparent from the following description of embodiments taken in conjunction with the accompanying drawings. Like parts are designated by like reference characters throughout the various figures of the drawings; reference characters that have already been assigned are omitted in subsequent figures if this contributes to clarity. In the drawings.

DETAILED DESCRIPTION OF EXEMPLARY EMBODIMENTS

Figure 1:
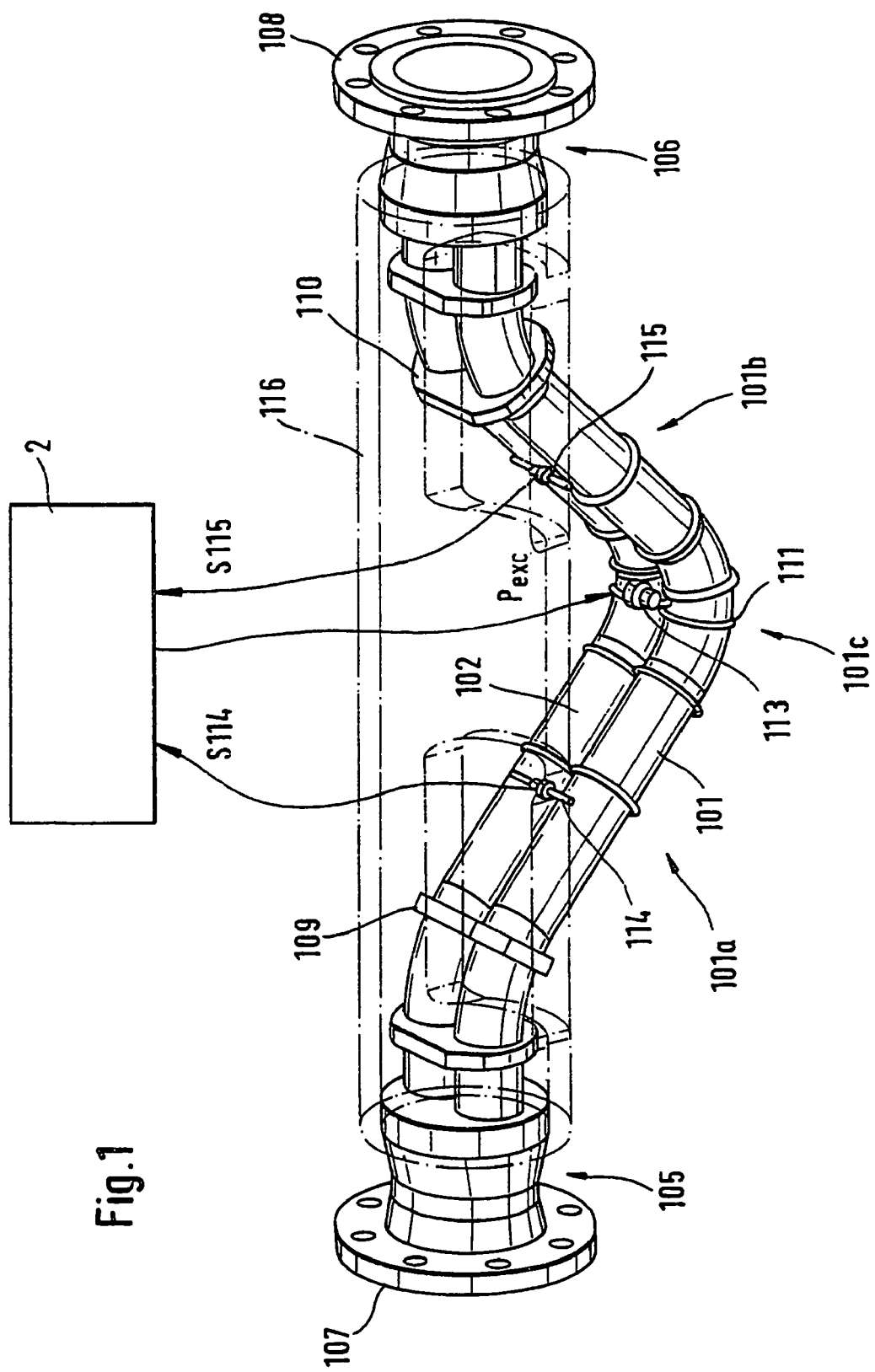
FIG. 1 is a perspective view of a first variant of a vibratory transducer especially suited for use in a Coriolis mass flowmeter or a Coriolis mass flowmeter-densimeter.

While the invention is susceptible to various modifications and alternative forms, exemplary embodiments thereof have been shown by way of example in the drawings and will herein be described in detail. It should be understood, however, that there is no intent to limit the invention to the the particular forms diclosed, but on the contrary, the intention is to cover all modifications, equivalents, and alternatives falling within the spirit and scope of the invention as defined by the intended claims.

Figure 2:
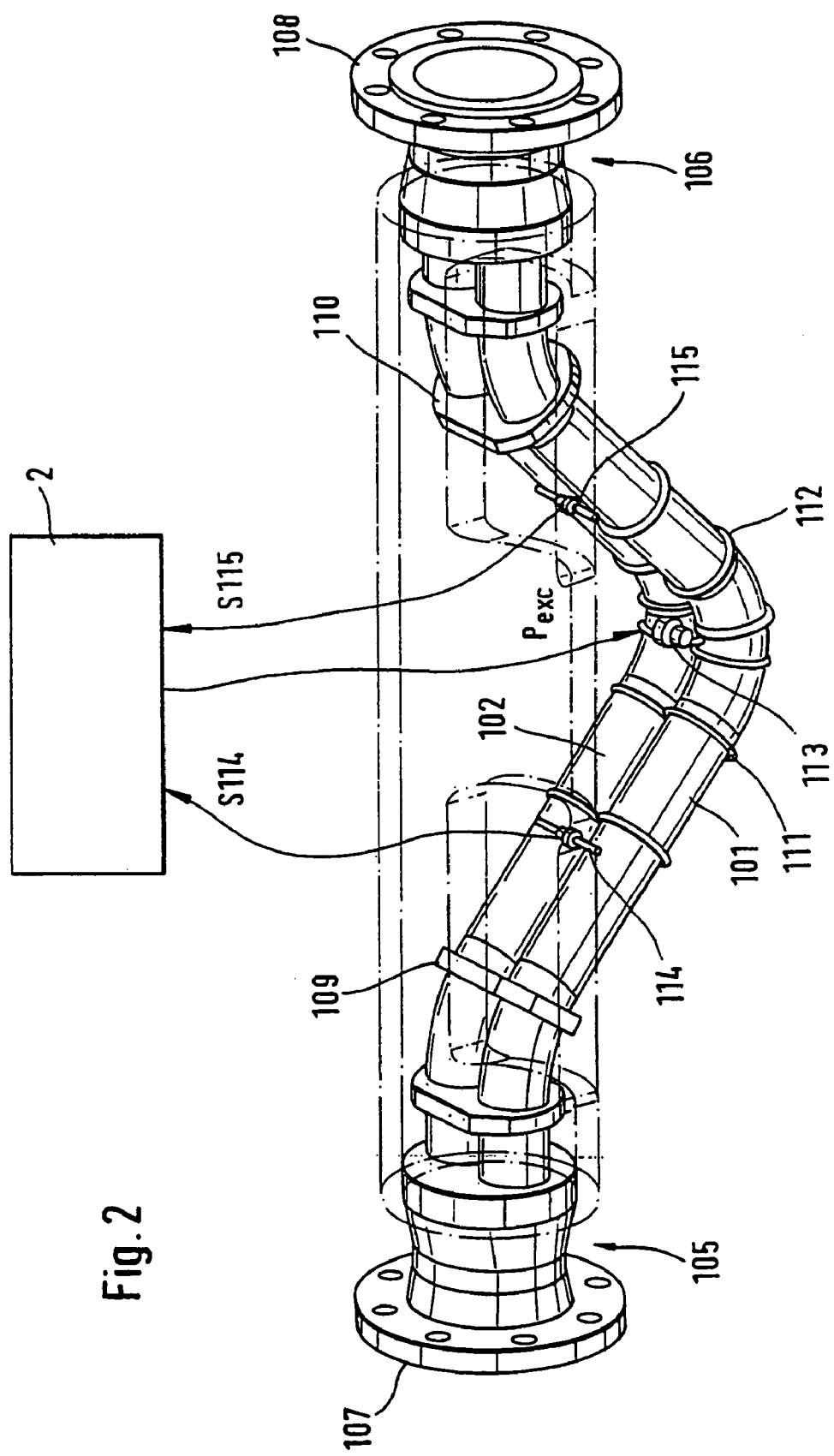
FIG. 2 is a perspective view of a second variant of a vibratory transducer especially suited for use in a Coriolis mass flowmeter or a Coriolis mass flowmeter-densimeter.

FIGS. 1 and 2 show embodiments of a vibratory transducer 1 which responds in particular to the mass flow rate of a fluid flowing in a pipe (not shown). If used in a Coriolis mass flowmeter, for example, the transducer will serve to produce Coriolis forces in the fluid flowing therethrough and to sense these forces and convert them into measurement signals suitable for electronic evaluation.

To conduct the fluid to be measured, transducer 1 comprises a curved first flow tube 101 of predeterminable lumen. Flow tube 101, as is readily apparent from FIGS. 1 to 3, has a first straight tube segment 101a on the inlet side and a second straight tube segment 101b on the outlet side. The two straight tube segments are connected by an arcuate, e.g., circular-arc-shaped, tube segment 101c of predeterminable three-dimensional shape, preferably in such an alignment relative to each other that flow tube 101 spreads a plane surface. Materials suitable for flow tube 101 are practically all materials conventionally used for such flow tubes, like special-steel, titanium, tantalum, or zirconium alloys.

Flow tube 101 is preferably bent into a U-shape or, as shown in FIG. 1, into a V-shape, as is also described in EP-A 1 154 243. Further suitable three-dimensional shapes for flow tube 101 are shown, for example, in the above referred to U.S. Pat. No. 5,731,527, U.S. Pat. No. 5,301,557, U.S. Pat. No. 4,895,030, WO-A 01/33174, or WO-A 00/57141.

Figure 3:
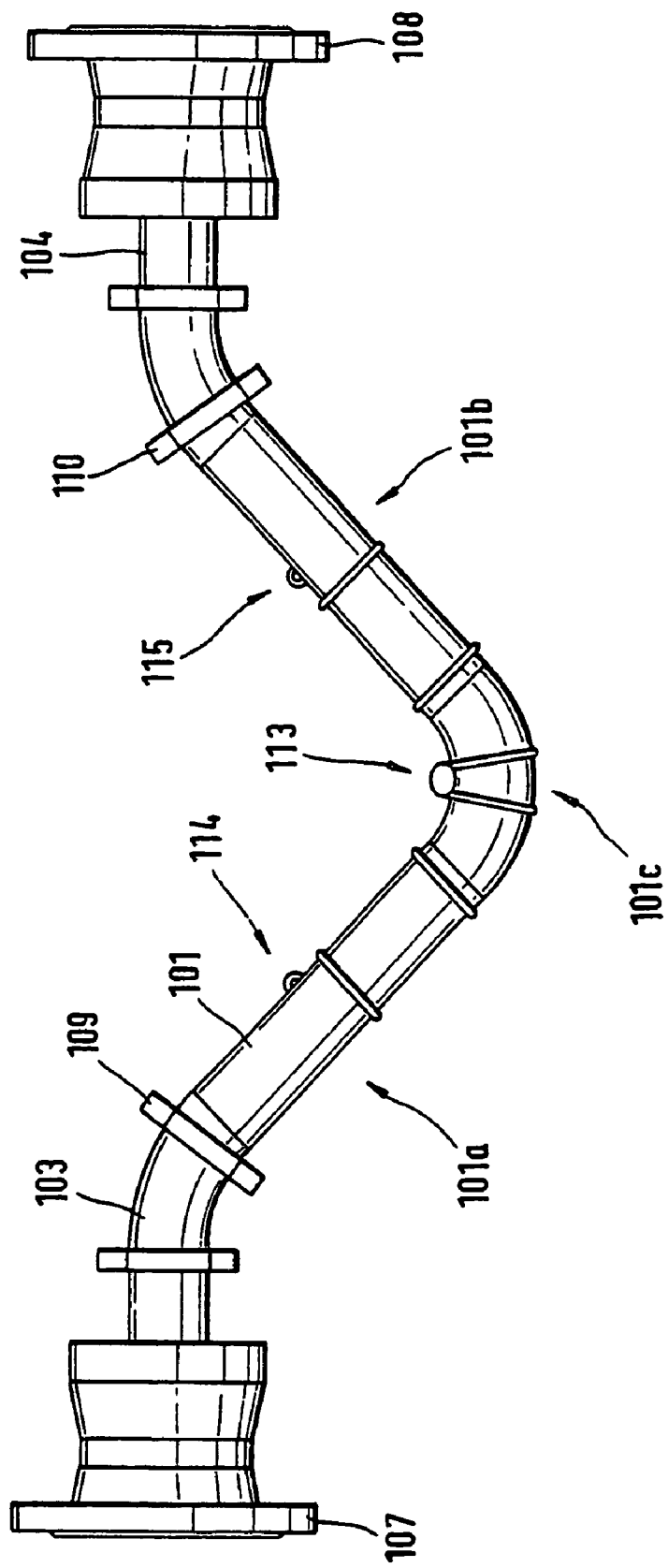
FIG. 3 is a side view of a flow tube of the transducer of FIG. 1 and/or FIG. 2.

As shown in FIGS. 1 to 3, flow tube 101 has an inlet tube section 103, ending in an inlet end, and an outlet tube section 104, ending in an outlet end. If the meter is installed in a pipe, inlet tube section 103 and outlet tube section 104 will be connected with an inlet-side section and an outlet-side section, respectively, of the fluid-carrying and usually straight pipe. The two tube sections 103, 104 are therefore preferably in alignment with an imaginary longitudinal axis $A_1$ joining the two.

Preferably, flow tube 101 and the inlet and outlet tube sections 103, 104 are formed from a single tubular semifinished product of suitable length. The semifinished product may be brought to the desired shape in the manner familiar to those skilled in the art, e.g., by mandrel bending or press bending, and then cut to the necessary length.

If the transducer is to be detachably mounted in the pipe, a first flange 107 and a second flange 108 will preferably be formed on inlet tube section 103 and outlet tube section 104, respectively. If necessary, however, inlet tube section 103 and outlet tube section 104 may also be secured to the pipe directly, e.g., by welding or brazing.

In addition to the first flow tube 101, transducer 1, in the embodiment shown, comprises a second flow tube 102, which is preferably identical to flow tube 101; the second flow tube 102 is not absolutely necessary, i.e., the transducer, as also described in U.S. Pat. No. 5,549,009 and in European Application 01 11 2546.5, which was not published prior to the filing date of the present application, may comprise only a single curved flow tube.

As is usual with such transducers with a double flow tube configuration, in the transducer of the embodiment, inlet tube section 103 ends in an inlet manifold 105, and outlet tube section 104 ends in a corresponding outlet manifold 106, so that in operation, flow tube 101 will communicate with the connected pipe via inlet and outlet tube sections 103, 104 and inlet and outlet manifolds 105, 106. Flow tube 102 is also connected with the pipe via inlet and outlet manifolds 105, 106.

Preferably, transducer 1 has a support frame 116 for holding flow tube 101 or flow tubes 101, 102. Support frame 116 has a cover (not shown) for tube segments protruding therefrom.

In operation, the two flow tubes 101, 102 are excited in a useful mode into flexural vibrations about an axis of vibration essentially parallel to the longitudinal axis $A_1$ of the transducer, particularly at a natural resonance frequency of an eigenmode, such that, as is usual with such transducers, flow tube 101 will oscillate predominantly in antiphase to flow tube 102, at least in the areas of tube segments 101a, 101b, 101c. The Coriolis forces induced thereby in the fluid flowing through flow tubes 101, 102, as is well known, cause an additional elastic deformation of flow tubes 101, 102 which is also dependent on the mass flow rate to be measured, and which is superimposed on the deformations of flow tubes 101, 102 caused by the flexural vibrations of the useful mode. At this point it should be emphasized again that during the vibrations of flow tube 101, particularly during the flexural vibrations in the useful mode, each of tube segments 101a, 101b, 101c is laterally displaced at least in sections and, in the process, elastically deformed at least in sections, e.g., slightly bent out and/or twisted.

If necessary, any mechanical stresses caused by the vibrating flow tubes 101, 102 in inlet tube section 103 and outlet tube section 104 can be minimized, for example, by connecting flow tubes 101, 102 by means of at least a first node plate 109 on the inlet side and at least a second node plate 110 on the outlet side, as is usual with such transducers.

To drive the flow tubes 101, 102, transducer 1 comprises at least one vibration exciter 113. The latter serves to convert electric excitation power $P_{exc}$ supplied from a suitable measuring and control circuit 2, e.g., a circuit of the above-mentioned Coriolis mass flowmeter, into excitation forces, e.g., pulsating or harmonic forces, which act on flow tubes 101, 102 symmetrically, i.e., simultaneously, and uniformly but in opposite directions, thus producing antiphase vibrations of flow tubes 101, 102. The excitation forces can be adjusted in amplitude, e.g., by means of a current- and/or voltage-regulator circuit, and in frequency, e.g., by means of a phase-locked loop, in the manner familiar to those skilled in the art; see also U.S. Pat. No. 4,801,897. It should be noted that measuring and control circuit 2 is housed in a suitable electronics case (not shown) which may be mounted directly to or located remote from the transducer, for example.

To sense vibrations of the vibrating flow tubes 101, 102, transducer 1 has an inlet-side first vibration sensor 114 and an outlet-side second vibration sensor 115. The two vibration sensors 114, 115 respond to motions of flow tubes 101, 102, particularly to lateral deflections and/or deformations of the tubes, and provide corresponding first and second vibration signals $s_{114}$ and $s_{115}$, respectively. The two vibration sensors are prefereabley identical in construction; they may also be essentially identical in construction to vibration exciter 113.

As mentioned, the flexural vibrations in the useful mode alone cause an elastic deformation of flow tube 101, at least of sections of the tube. This deformation affects in particular the three-dimensional shape of the arcuate tube segment 101c and, hence, the shape of the tube lumen in this area, particularly the cross section.

The deformation of flow tube 101, particularly the deformation of the arcuate tube segment 101c, may differ depending on the respective static internal pressure in flow tube 1 or on a corresponding pressure distribution. If the internal pressure or the pressure distribution varies, for example, these different deformations may result in the Coriolis forces produced by the useful mode differing in magnitude despite an unchanged mass flow rate, i.e., conventional transducers of the kind described can also exhibit a cross sensitivity to pressure, particularly to static pressure, which is not negligibly high.

To the inventors' surprise it turned out that this cross sensitivity is due largely to the pressure-dependent change of the three-dimensional shape of the flow tube in the relatively small areas of arcuate tube segments, particularly to section changes.

According to the invention at least a first stiffening element 111 is provided for flow tube 101 to eliminate or at least reduce this cross sensitivity of transducer 1 and, thus, to reduce cross talks from pressure to mass flow corresponding Coriolis forces. As shown in FIG. 1 or 2, this stiffening element 111 is fixed on flow tube 101 in the area of the arcuate tube segment 101c. Stiffening element 111 serves to stabilize the three-dimensional shape, particularly a cross-sectional shape, of the oscillating tube segment 101c such that the latter, despite a varying static pressure in the lumen of the flow tube, will respond to a virtually constant mass flow rate in nearly the same manner with a change of its three-dimensional shape. For this purpose, stiffening element 111 is fixed to flow tube 101 in such a way that compared to identically shaped conventional flow tubes without such a stiffening element, the lateral vibratory motions of flow tube 101 are left essentially unaffected.

Accordingly, stiffening element 111 is fixed only to flow tube 101, so that unlike the node plates 109, 110, for example, it does not counteract the vibrations of flow tube 101 except for its mass inertia, which is kept to a minimum. In other words, for the purpose of stabilizing the three-dimensional shape of tube segment 101c, stiffening element 111 should be linked neither with any second flow tube 102 nor with support frame 116, e.g., via elastic and/or damping elements, so that flow tube 101, and particularly its segments 101a, 101b, 101c, can still vibrate essentially freely. If necessary, however, stiffening element 111 may also serve as a holder for vibration exciter 113, for example, as indicated in FIGS. 1 and 2.

The materials used for stiffening element 111 may, for instance, be the same as those used for flow tube 101. Since stiffening element 111 does not come into contact with the fluid, a metal or metal alloy of lower quality than that used for flow tube 101, for example, would also be sufficient, provided, of course, that it is compatible, e.g., in its thermal characteristic, with the material chosen for flow tube 101.

In a preferred embodiment of the invention, stiffening element 111 is annular in shape and is fixed to flow tube 101 in such a way that the latter, as indicated in FIGS. 1 and 2, is encompassed and particularly embraced by stiffening element 111, preferably essentially coaxially.

Particularly if stiffening 111 is annular in shape, it may be fitted on flow tube 101 by thermal shrinking, for example. It may also be slipped over flow tube 101 and attached to the latter by welding or soldering, particularly by brazing, for example, or be formed on or machined from the above-mentioned tubular semifinished product during manufacture of the same. In other words, the at least one stiffening element 111 is preferably fixed to flow tube 101 in such a manner that it can counteract even tose, particularly pressure-fluctuations- or low-pressure-induced, forces or stresses in flow tube 101 which otherwise would result in undesired deformations or, particularly radial, distortions of cross section, along with partial reductions of the diameter of tube segment 101c.

According to a preferred first variant of the invention, the at least one stiffening element 111 is provided directly on the arcuate tube segment 101c of flow tube 101, see FIG. 1.

According to a preferred second variant of the invention, stiffening element 111 is provided on the inlet-side straight tube segment 101a in the vicinity of the arcuate tube segment 101c, see FIG. 2. At least in this variant of the invention, the transducer further comprises a second stiffening element 112 for flow tube 101, which is essentially identical to stiffening element 111. The second stiffening element 112, as shown in FIG. 2, is preferably fixed on the straight tube segment 101b, also in proximity to the arcuate tube segment 101c, particularly at the same distance from the middle of the flow tube as stiffening element 111. As is readily apparent from FIG. 1, however, two stiffening elements 111, 112 may also be provided for the arcuate tube segment 101c in the above-mentioned first variant.

Investigations have also shown that use of stiffening element 111 has a particularly favorable effect on reduction of cross talk from pressure to masse flow corresponding Coriolis forces if flow tube 101 has an inside diameter well over 40 mm, particularly over 50 mm.

A further advantage of the invention lies in the fact that such stiffening elements can be readily retrofitted at low cost to existing transducer designs or to types of transducers that are already in production, whereby even in the case of conventional types of Coriolis mass flowmeters, measurement accuracy can be substantially improved in a simple manner.

While the invention has been illustrated and described in detail in the drawings and forgoing description, such illustration and description is to be considered as exemplary not restrictive in character, it being understood that only exemplary embodiments have been shown and described and that all changes and modifications that come within the spirit and scope of the invention as described herein are desired to protected.

What is claimed is:

1. A vibratory transducer, comprising:
   at least one curved flow tube serving to conduct a fluid, said at least one flow tube including at least one arcuate tube segment which adjoins a first straight tube segment on the inlet side and a second straight tube segment on the outlet side, such that said flow tube is bent in a U-shape or a V-shape; and
   at least a first stiffening element fixed on the first straight tube segment and at least a second stiffening element fixed on the second straight tube segment, each of said first and second stiffening elements being adapted to reduce a cross sensitivity of the transducer to pressure.

2. The vibratory transducer as claimed in claim 1, wherein said at least first stiffening element is annular in shape and is fixed to said flow tube so as to encompass said flow tube.

3. The vibratory transducer as claimed in claim 2 wherein said at least first stiffening element encompasses said flow tube essentially coaxially.

4. A vibratory transducer comprising:
   at least one curved flow tube which communicates with a connected pipe conducting a fluid to be measured, said at least one flow tube including a first straight tube segment, a second straight tube segment, and at least one arcuate tube segment, said at least one arcuate tube segment adjoining said first straight tube segment and said second straight tube segment;
   at least one vibration exciter for driving said at least one flow tube to perform vibrations;
   vibration sensors for sensing vibrations of said at least one flow tube; and
   at least one annular stiffening element fixed on said at least one curved flow tube so as to encompass the at least one curved flow tube, said at least one stiffening element being fixed to said at least one arcuate tube segment or in the vicinity thereof.

5. The vibratory transducer as claimed in claim 4, wherein the at least one flow tube is bent in a U-shape.

6. The vibratory transducer as claimed in claim 4, wherein the at least one flow tube is bent in a V-shape.

7. The vibratory transducer as claimed in claim 4, wherein a material of said flow tube is special-steel.

8. The vibratory transducer as claimed in claim 4, wherein a material of said flow tube is selected from a group consisting of titanium, tantalum, and zirconium alloys.

9. The vibratory transducer as claimed in claim 4, wherein the stiffening element is made from metal.

10. The vibratory transducer as claimed in claim 4, wherein a material of said stiffening element is the same as a material of the flow tube.

11. The vibratory transducer as claimed in claim 10, wherein the stiffening element is made from metal, and wherein the at least one stiffening element is fitted on said flow tube by brazing.

12. The vibratory transducer as claimed in claim 11, wherein a material of said flow tube is special-steel.

13. The vibratory transducer as claimed in claim 4, wherein the flow tube has an inside diameter of more than 40 mm.

14. A vibratory transducer, comprising:
   a curved first flow tube and a curved second flow tube, each of said first and second flow tubes includes a first straight tube segment, a second straight tube segment, and at least one arcuate tube segment adjoining said first and second straight tube segments;
   a inlet manifold and a outlet manifold, each of said inlet and outlet manifolds is connected with said first and second flow tubes;
   at least one vibration exciter for driving said first and second flow tubes tube to perform vibrations;
   vibration sensors for sensing vibrations of said first and second flow tubes; and
   at least one stiffening element fixed only to the first flow tube on said at least one arcuate tube segment.

15. The vibratory transducer as claimed in claim 14, wherein each of said first and second flow tubes is bent in a U-shape.

16. The vibratory transducer as claimed in claim 14, wherein each of said first and second flow tubes is bent in a V-shape.

17. The vibratory transducer as claimed in claim 14, wherein the stiffening element is made from metal.

18. The vibratory transducer as claimed in claim 14, wherein a material of said first flow tube is selected from a group consisting of titanium, tantalum, and zirconium alloys.

19. The vibratory transducer as claimed in claim 14, wherein a material of said first flow tube is special-steel.

20. The vibratory transducer as claimed in claim 19, wherein the stiffening element is made from metal.

21. The vibratory transducer as claimed in claim 20, wherein the stiffening element is made from metal, and wherein the at least one stiffening element is fitted on said first flow tube by brazing.

22. The vibratory transducer as claimed in claim 14, wherein a material of said stiffening element is the same as a material of the first flow tube.

23. The vibratory transducer as claimed in claim 22, wherein the stiffening element is made from metal, and wherein the at least one stiffening element is fitted on said first flow tube by brazing.

24. The vibratory transducer as claimed in claim 14, wherein the second flow tube is identical to said first flow tube.

25. A vibratory transducer, comprising:

a curved first flow tube and a curved second flow tube, each of said first and second flow tubes includes a first straight tube segment, a second straight tube segment, and at least one arcuate tube segment adjoining said first and second straight tube segments;

a inlet manifold and a outlet manifold, each of said inlet and outlet manifolds is connected with said first and second flow tubes;

at least one vibration exciter for driving said first and second flow tubes tube to perform vibrations;

vibration sensors for sensing vibrations of said first and second flow tubes; and a first stiffening element and a second stiffing element, each of said first and second stiffing elements being fixed only to the first flow tube in the vicinity of said at least one arcuate tube segment.

* * * * *